(12) United States Patent
Chee et al.

(10) Patent No.: US 11,219,479 B2
(45) Date of Patent: Jan. 11, 2022

(54) INTEGRITY TESTING METHOD AND APPARATUS FOR DELIVERING VAPOR TO THE UTERUS

(71) Applicant: AEGEA MEDICAL INC., Menlo Park, CA (US)

(72) Inventors: Uriel Hiram Chee, Santa Cruz, CA (US); Robert Bilgor Peliks, San Francisco, CA (US); Hugh Edward Magen, Belmont, CA (US); Donnell William Gurskis, Belmont, CA (US); Steven Robert Bacich, Half Moon Bay, CA (US)

(73) Assignee: Aegea Medical Inc., Menlo Park, CA (US)

(*) Notice: Subject to any disclaimer, the term of this patent is extended or adjusted under 35 U.S.C. 154(b) by 3 days.

(21) Appl. No.: 16/248,292

(22) Filed: Jan. 15, 2019

(65) Prior Publication Data

US 2019/0142496 A1    May 16, 2019

Related U.S. Application Data

(62) Division of application No. 14/719,037, filed on May 21, 2015, now Pat. No. 10,179,019.
(Continued)

(51) Int. Cl.
*A61B 18/04* (2006.01)
*A61B 5/00* (2006.01)
(Continued)

(52) U.S. Cl.
CPC .............. *A61B 18/04* (2013.01); *A61B 5/035* (2013.01); *A61B 5/4325* (2013.01);
(Continued)

(58) Field of Classification Search
CPC ............ A61B 17/42; A61B 2017/4216; A61B 5/4325; A61B 5/6847; A61B 18/04;
(Continued)

(56) References Cited

U.S. PATENT DOCUMENTS

| 408,899 A | 8/1889 | Small |
| 697,181 A | 4/1902 | Smith |

(Continued)

FOREIGN PATENT DOCUMENTS

| CN | 201189204 Y | 2/2009 |
| CN | 201379631 Y | 1/2010 |

(Continued)

OTHER PUBLICATIONS

Baker et al.; Threshold intrauterine perfusion pressures for intraperitoneal spill during hydrotubation and correlation with tubal adhesive diseases; Fertility and Sterility; 64(6); pp. 1066-1069; Dec. 31, 1995.
(Continued)

*Primary Examiner* — Tammie K Marlen
(74) *Attorney, Agent, or Firm* — Fish & Richardson P.C.

(57) ABSTRACT

A method and system of providing therapy to a patient's uterus is provided, which can include any number of features. The method can include the steps of inserting a uterine device into the uterus and performing a uterine integrity test to determine that the uterus is intact and not perforated. If it is determined that the uterus is not perforated, a patency test can be performed to determine that the uterine device is not clogged or embedded in tissue. If the uterus is intact and the device is not clogged or embedded in tissue, the uterus can be treated with the uterine device, e.g., uterine ablation. Systems for performing these methods are also disclosed.

7 Claims, 6 Drawing Sheets

Related U.S. Application Data

(60) Provisional application No. 62/002,070, filed on May 22, 2014.

(51) Int. Cl.
| | |
|---|---|
| *A61B 17/42* | (2006.01) |
| *A61B 5/03* | (2006.01) |
| *A61M 31/00* | (2006.01) |
| *A61M 25/04* | (2006.01) |
| *A61B 90/00* | (2016.01) |
| *A61B 17/00* | (2006.01) |
| *A61M 25/10* | (2013.01) |
| *A61B 18/00* | (2006.01) |

(52) U.S. Cl.
CPC ............ *A61B 5/6847* (2013.01); *A61B 17/42* (2013.01); *A61M 25/04* (2013.01); *A61M 31/00* (2013.01); *A61B 2017/00022* (2013.01); *A61B 2017/00115* (2013.01); *A61B 2017/00557* (2013.01); *A61B 2017/4216* (2013.01); *A61B 2018/00559* (2013.01); *A61B 2090/064* (2016.02); *A61B 2090/0807* (2016.02); *A61M 2025/1052* (2013.01); *A61M 2210/1433* (2013.01)

(58) Field of Classification Search
CPC .... A61B 2018/00577; A61B 2018/048; A61B 5/035; A61B 2090/064; A61B 2090/0807; A61B 2017/00022; A61B 2017/00115; A61B 2017/00557; A61B 2018/00559; A61M 25/04; A61M 31/00; A61M 2210/1433
See application file for complete search history.

(56) References Cited

U.S. PATENT DOCUMENTS

| | | | |
|---|---|---|---|
| 1,719,750 | A | 7/1929 | Bridge et al. |
| 3,818,913 | A | 6/1974 | Wallach |
| 3,871,374 | A | 3/1975 | Bolduc et al. |
| 3,880,168 | A | 4/1975 | Berman |
| 3,924,628 | A | 12/1975 | Droegemueller et al. |
| 3,930,505 | A | 1/1976 | Wallach |
| 4,083,077 | A | 4/1978 | Knight et al. |
| 4,447,227 | A | 5/1984 | Kotsanis |
| 4,672,962 | A | 6/1987 | Hershenson |
| 4,682,596 | A | 7/1987 | Bales et al. |
| 4,748,979 | A | 6/1988 | Hershenson |
| 4,773,410 | A | 9/1988 | Blackmer et al. |
| 4,793,352 | A | 12/1988 | Eichenlaub |
| 4,872,920 | A | 10/1989 | Flynn et al. |
| 4,898,574 | A | 2/1990 | Uchiyama et al. |
| 4,915,113 | A | 4/1990 | Holman |
| 4,941,475 | A | 7/1990 | Williams et al. |
| 4,950,266 | A | 8/1990 | Sinofsky |
| 4,976,711 | A | 12/1990 | Parins et al. |
| 4,985,027 | A | 1/1991 | Dressel |
| 5,006,119 | A | 4/1991 | Acker et al. |
| 5,011,566 | A | 4/1991 | Hoffman |
| 5,045,056 | A | 9/1991 | Behl |
| 5,078,736 | A | 1/1992 | Behl |
| 5,084,043 | A | 1/1992 | Hertzmann et al. |
| 5,084,044 | A | 1/1992 | Quint |
| 5,102,410 | A | 4/1992 | Dressel |
| 5,112,328 | A | 5/1992 | Taboada et al. |
| 5,122,138 | A | 6/1992 | Manwaring |
| 5,145,935 | A | 9/1992 | Hayashi |
| 5,158,536 | A | 10/1992 | Sekins et al. |
| 5,162,374 | A | 11/1992 | Mulieri et al. |
| 5,190,539 | A | 3/1993 | Fletcher et al. |
| 5,217,459 | A | 6/1993 | Kamerling |
| 5,217,465 | A | 6/1993 | Steppe |
| 5,218,970 | A | 6/1993 | Turnbull et al. |
| 5,242,474 | A | 9/1993 | Herbst et al. |
| 5,246,436 | A | 9/1993 | Rowe |
| 5,263,951 | A | 11/1993 | Spears et al. |
| 5,277,201 | A | 1/1994 | Stern |
| 5,277,696 | A | 1/1994 | Hagen |
| 5,306,274 | A | 4/1994 | Long |
| 5,318,014 | A | 6/1994 | Carter |
| 5,331,947 | A | 7/1994 | Shturman |
| 5,334,190 | A | 8/1994 | Seiler |
| 5,344,397 | A | 9/1994 | Heaven et al. |
| 5,348,551 | A | 9/1994 | Spears et al. |
| 5,352,512 | A | 10/1994 | Hoffman |
| 5,411,482 | A | 5/1995 | Campbell |
| 5,417,686 | A | 5/1995 | Peterson et al. |
| 5,424,620 | A | 6/1995 | Cheon et al. |
| 5,433,708 | A | 7/1995 | Nichols et al. |
| 5,433,739 | A | 7/1995 | Sluijter et al. |
| 5,437,629 | A | 8/1995 | Goldrath |
| 5,443,470 | A | 8/1995 | Stern et al. |
| 5,445,168 | A | 8/1995 | Krebs |
| 5,449,380 | A | 9/1995 | Chin |
| 5,451,208 | A | 9/1995 | Goldrath |
| 5,462,521 | A | 10/1995 | Brucker et al. |
| 5,500,012 | A | 3/1996 | Brucker et al. |
| 5,503,638 | A | 4/1996 | Cooper et al. |
| 5,505,730 | A | 4/1996 | Edwards |
| 5,506,300 | A | 4/1996 | Ward et al. |
| 5,524,620 | A | 6/1996 | Rosenschein |
| 5,529,076 | A | 6/1996 | Schachar |
| 5,540,658 | A | 7/1996 | Evans et al. |
| 5,542,928 | A | 8/1996 | Evans et al. |
| 5,554,172 | A | 9/1996 | Horner et al. |
| 5,562,608 | A | 10/1996 | Sekins et al. |
| 5,562,720 | A | 10/1996 | Stern et al. |
| 5,584,872 | A | 12/1996 | LaFontaine et al. |
| 5,591,157 | A | 1/1997 | Hennings et al. |
| 5,616,120 | A | 4/1997 | Andrew et al. |
| 5,620,440 | A | 4/1997 | Heckele et al. |
| 5,647,871 | A | 7/1997 | Levine et al. |
| 5,653,692 | A | 8/1997 | Masterson et al. |
| 5,662,671 | A | 9/1997 | Barbut et al. |
| 5,665,074 | A | 9/1997 | Kelly |
| 5,665,822 | A | 9/1997 | Bitler et al. |
| 5,669,907 | A | 9/1997 | Platt et al. |
| 5,674,191 | A | 10/1997 | Edwards et al. |
| 5,681,282 | A | 10/1997 | Eggers et al. |
| 5,683,366 | A | 11/1997 | Eggers et al. |
| 5,688,267 | A | 11/1997 | Panescu et al. |
| 5,695,507 | A | 12/1997 | Auth et al. |
| 5,697,281 | A | 12/1997 | Eggers et al. |
| 5,697,536 | A | 12/1997 | Eggers et al. |
| 5,697,882 | A | 12/1997 | Eggers et al. |
| 5,697,909 | A | 12/1997 | Eggers et al. |
| 5,700,262 | A | 12/1997 | Acosta et al. |
| 5,707,352 | A | 1/1998 | Sekins et al. |
| 5,730,719 | A | 3/1998 | Edwards |
| 5,735,811 | A | 4/1998 | Brisken |
| 5,741,247 | A | 4/1998 | Rizoiu et al. |
| 5,741,248 | A | 4/1998 | Stern et al. |
| 5,743,870 | A | 4/1998 | Edwards |
| 5,752,965 | A | 5/1998 | Francis et al. |
| 5,754,717 | A | 5/1998 | Esch |
| 5,755,753 | A | 5/1998 | Knowlton |
| 5,769,880 | A | 6/1998 | Truckai et al. |
| 5,782,914 | A | 7/1998 | Schankereli |
| 5,785,521 | A | 7/1998 | Rizoiu et al. |
| 5,800,379 | A | 9/1998 | Edwards |
| 5,800,482 | A | 9/1998 | Pomeranz et al. |
| 5,800,493 | A | 9/1998 | Stevens et al. |
| 5,810,764 | A | 9/1998 | Eggers et al. |
| 5,820,580 | A | 10/1998 | Edwards et al. |
| 5,824,703 | A | 10/1998 | Clark |
| 5,827,268 | A | 10/1998 | Laufer |
| 5,836,896 | A | 11/1998 | Rosenschein |
| 5,836,906 | A | 11/1998 | Edwards |
| 5,843,019 | A | 12/1998 | Eggers et al. |
| 5,871,469 | A | 2/1999 | Eggers et al. |
| 5,873,855 | A | 2/1999 | Eggers et al. |

(56) References Cited

U.S. PATENT DOCUMENTS

| | | |
|---|---|---|
| 5,879,329 A | 3/1999 | Ginsburg |
| 5,885,243 A | 3/1999 | Capetan et al. |
| 5,888,198 A | 3/1999 | Eggers et al. |
| 5,891,094 A | 4/1999 | Masterson et al. |
| 5,891,095 A | 4/1999 | Eggers et al. |
| 5,891,134 A | 4/1999 | Goble et al. |
| 5,891,457 A | 4/1999 | Neuwirth |
| 5,902,272 A | 5/1999 | Eggers et al. |
| 5,911,734 A | 6/1999 | Tsugita et al. |
| 5,913,856 A | 6/1999 | Chia et al. |
| 5,938,660 A | 8/1999 | Swartz et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu et al. |
| 5,976,129 A | 11/1999 | Desai |
| 5,980,504 A | 11/1999 | Sharkey et al. |
| 5,986,662 A | 11/1999 | Argiro et al. |
| 5,989,212 A | 11/1999 | Sussman et al. |
| 5,989,249 A | 11/1999 | Kirwan |
| 5,989,445 A | 11/1999 | Wise et al. |
| 5,997,499 A | 12/1999 | Sussman et al. |
| 6,004,509 A | 12/1999 | Dey et al. |
| 6,015,406 A | 1/2000 | Goble et al. |
| 6,024,095 A | 2/2000 | Stanley |
| 6,024,733 A | 2/2000 | Eggers et al. |
| 6,027,501 A | 2/2000 | Goble et al. |
| 6,032,077 A | 2/2000 | Pomeranz |
| 6,045,532 A | 4/2000 | Eggers et al. |
| 6,045,549 A | 4/2000 | Smethers et al. |
| 6,047,700 A | 4/2000 | Eggers et al. |
| 6,053,172 A | 4/2000 | Hovda et al. |
| 6,053,909 A | 4/2000 | Shadduck |
| 6,056,746 A | 5/2000 | Goble et al. |
| 6,057,689 A | 5/2000 | Saadat |
| 6,059,011 A | 5/2000 | Giolo |
| 6,063,079 A | 5/2000 | Hovda et al. |
| 6,063,081 A | 5/2000 | Mulier et al. |
| 6,066,132 A | 5/2000 | Chen et al. |
| 6,066,134 A | 5/2000 | Eggers et al. |
| 6,066,139 A | 5/2000 | Ryan et al. |
| 6,080,128 A | 6/2000 | Sussman et al. |
| 6,080,151 A | 6/2000 | Swartz et al. |
| 6,083,255 A | 7/2000 | Laufer et al. |
| 6,086,585 A | 7/2000 | Hovda et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,105,581 A | 8/2000 | Eggers et al. |
| 6,106,516 A | 8/2000 | Massengill |
| 6,109,268 A | 8/2000 | Thapliyal et al. |
| 6,113,594 A | 9/2000 | Savage |
| 6,113,597 A | 9/2000 | Eggers et al. |
| 6,113,722 A | 9/2000 | Hoffman et al. |
| 6,117,109 A | 9/2000 | Eggers et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,160 A | 12/2000 | Hsei et al. |
| 6,159,194 A | 12/2000 | Eggers et al. |
| 6,159,207 A | 12/2000 | Yoon |
| 6,159,208 A | 12/2000 | Hovda et al. |
| 6,162,210 A | 12/2000 | Shadduck |
| 6,162,232 A | 12/2000 | Shadduck |
| 6,174,308 B1 | 1/2001 | Goble et al. |
| 6,179,805 B1 | 1/2001 | Sussman et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,203,542 B1 | 3/2001 | Ellsberry et al. |
| 6,210,402 B1 | 4/2001 | Olsen et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,228,078 B1 | 5/2001 | Eggers et al. |
| 6,228,081 B1 | 5/2001 | Goble |
| 6,228,082 B1 | 5/2001 | Baker et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,254,600 B1 | 7/2001 | Willink et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,277,112 B1 | 8/2001 | Underwood et al. |
| 6,277,114 B1 | 8/2001 | Bullivant et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,290,715 B1 | 9/2001 | Sharkey et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,299,633 B1 | 10/2001 | Laufer |
| 6,300,150 B1 | 10/2001 | Venkatasubramanian |
| 6,306,129 B1 | 10/2001 | Little et al. |
| 6,306,134 B1 | 10/2001 | Goble et al. |
| 6,309,387 B1 | 10/2001 | Eggers et al. |
| 6,312,408 B1 | 11/2001 | Eggers et al. |
| 6,312,474 B1 | 11/2001 | Francis et al. |
| 6,315,755 B1 | 11/2001 | Sussman |
| 6,319,221 B1 | 11/2001 | Savage et al. |
| 6,322,549 B1 | 11/2001 | Eggers et al. |
| 6,327,505 B1 | 12/2001 | Medhkour et al. |
| 6,328,735 B1 | 12/2001 | Curley et al. |
| 6,331,171 B1 | 12/2001 | Cohen |
| 6,355,032 B1 | 3/2002 | Hovda et al. |
| 6,361,531 B1 | 3/2002 | Hissong |
| 6,363,937 B1 | 4/2002 | Hovda et al. |
| 6,364,877 B1 | 4/2002 | Goble et al. |
| 6,375,635 B1 | 4/2002 | Moutafis et al. |
| 6,379,350 B1 | 4/2002 | Sharkey et al. |
| 6,379,351 B1 | 4/2002 | Thapliyal et al. |
| 6,387,088 B1 | 5/2002 | Shadduck et al. |
| 6,388,043 B1 | 5/2002 | Langer et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,699 B1 | 6/2002 | Ash |
| 6,409,723 B1 | 6/2002 | Edwards |
| 6,425,877 B1 | 6/2002 | Edwards |
| 6,416,507 B1 | 7/2002 | Eggers et al. |
| 6,416,508 B1 | 7/2002 | Eggers et al. |
| 6,416,509 B1 | 7/2002 | Goble et al. |
| 6,425,867 B1 | 7/2002 | Vaezy et al. |
| 6,432,103 B1 | 8/2002 | Ellsberry et al. |
| 6,440,089 B1 | 8/2002 | Shine |
| 6,443,947 B1 | 9/2002 | Marko et al. |
| 6,451,012 B2 | 9/2002 | Dobak, III |
| 6,458,231 B1 | 10/2002 | Wapner et al. |
| 6,461,350 B1 | 10/2002 | Underwood et al. |
| 6,461,354 B1 | 10/2002 | Olsen et al. |
| 6,464,694 B1 | 10/2002 | Massengill |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,475,215 B1 | 11/2002 | Tanrisever |
| 6,482,201 B1 | 11/2002 | Olsen et al. |
| 6,488,673 B1 | 12/2002 | Laufer et al. |

(56) References Cited

U.S. PATENT DOCUMENTS

| | | |
|---|---|---|
| 6,493,589 B1 | 12/2002 | Medhkour et al. |
| 6,500,173 B2 | 12/2002 | Underwood et al. |
| 6,508,816 B2 | 1/2003 | Shadduck |
| 6,510,854 B2 | 1/2003 | Goble |
| 6,517,533 B1 | 2/2003 | Swaminathan |
| 6,522,930 B1 | 2/2003 | Schaer et al. |
| 6,527,761 B1 | 3/2003 | Soltesz et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,261 B2 | 4/2003 | Ellsberry et al. |
| 6,547,784 B1 | 4/2003 | Thompson et al. |
| 6,551,271 B2 | 4/2003 | Nguyen |
| 6,551,274 B2 | 4/2003 | Heiner |
| 6,554,780 B1 | 4/2003 | Sampson et al. |
| 6,557,559 B1 | 5/2003 | Eggers et al. |
| 6,558,379 B1 | 5/2003 | Batchelor et al. |
| 6,565,561 B1 | 5/2003 | Goble et al. |
| 6,569,146 B1 | 5/2003 | Werner et al. |
| 6,575,929 B2 | 6/2003 | Sussman et al. |
| 6,575,933 B1 | 6/2003 | Wittenberger et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,237 B2 | 7/2003 | Woloszko et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,610,043 B1 | 8/2003 | Ingenito |
| 6,620,155 B2 | 9/2003 | Underwood et al. |
| 6,623,444 B2 | 9/2003 | Babaev |
| 6,626,855 B1 | 9/2003 | Weng et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,634,363 B1 | 10/2003 | Danek et al. |
| 6,653,525 B2 | 11/2003 | Ingenito et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,692,490 B1 | 2/2004 | Edwards |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,708,056 B2 | 3/2004 | Duchon et al. |
| 6,712,811 B2 | 3/2004 | Underwood et al. |
| 6,712,812 B2 | 3/2004 | Roschak et al. |
| 6,719,754 B2 | 4/2004 | Underwood et al. |
| 6,726,684 B1 | 4/2004 | Woloszko et al. |
| 6,726,708 B2 | 4/2004 | Lasheras |
| 6,743,184 B2 | 6/2004 | Sampson et al. |
| 6,743,197 B1 | 6/2004 | Edwards |
| 6,746,447 B2 | 6/2004 | Davison et al. |
| 6,749,604 B1 | 6/2004 | Eggers et al. |
| 6,755,794 B2 | 6/2004 | Soukup |
| 6,758,846 B2 | 7/2004 | Goble et al. |
| 6,763,836 B2 | 7/2004 | Tasto et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,813,520 B2 | 11/2004 | Truckai et al. |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,872,183 B2 | 3/2005 | Sampson et al. |
| 6,875,194 B2 | 4/2005 | MacKool |
| 6,896,672 B1 | 5/2005 | Eggers et al. |
| 6,896,674 B1 | 5/2005 | Woloszko et al. |
| 6,896,675 B2 | 5/2005 | Leung et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,915,806 B2 | 7/2005 | Pacek et al. |
| 6,918,903 B2 | 7/2005 | Bass |
| 6,921,385 B2 | 7/2005 | Clements et al. |
| 6,929,640 B1 | 8/2005 | Underwood et al. |
| 6,929,642 B2 | 8/2005 | Xiao et al. |
| 6,949,096 B2 | 9/2005 | Davison et al. |
| 6,955,675 B2 | 10/2005 | Jain |
| 6,960,204 B2 | 11/2005 | Eggers et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |
| 6,991,028 B2 | 1/2006 | Comeaux et al. |
| 6,991,631 B2 | 1/2006 | Woloszko et al. |
| 7,004,940 B2 | 2/2006 | Ryan et al. |
| 7,004,941 B2 | 2/2006 | Tvinnereim et al. |
| 7,022,088 B2 | 4/2006 | Keast et al. |
| 7,022,105 B1 | 4/2006 | Edwards |
| 7,031,504 B1 | 4/2006 | Argiro et al. |
| 7,063,670 B2 | 6/2006 | Sampson et al. |
| 7,070,596 B1 | 7/2006 | Woloszko et al. |
| 7,083,612 B2 | 8/2006 | Littrup et al. |
| 7,094,215 B2 | 8/2006 | Davison et al. |
| 7,094,249 B1 | 8/2006 | Broome et al. |
| 7,101,367 B2 | 9/2006 | Xiao et al. |
| 7,104,986 B2 | 9/2006 | Hovda et al. |
| 7,105,007 B2 | 9/2006 | Hibler |
| RE39,358 E | 10/2006 | Goble |
| 7,128,748 B2 | 10/2006 | Mooradian et al. |
| 7,131,969 B1 | 11/2006 | Hovda et al. |
| 7,136,064 B2 | 11/2006 | Zuiderveld |
| 7,144,402 B2 | 12/2006 | Kuester |
| 7,144,588 B2 | 12/2006 | Gray et al. |
| 7,162,303 B2 | 1/2007 | Levin et al. |
| 7,169,143 B2 | 1/2007 | Eggers et al. |
| 7,179,255 B2 | 2/2007 | Lettice et al. |
| 7,186,234 B2 | 3/2007 | Dahla et al. |
| 7,192,400 B2 | 3/2007 | Campbell et al. |
| 7,192,428 B2 | 3/2007 | Eggers et al. |
| 7,201,750 B1 | 4/2007 | Eggers et al. |
| 7,217,268 B2 | 5/2007 | Eggers et al. |
| 7,233,820 B2 | 6/2007 | Gilboa |
| 7,235,070 B2 | 6/2007 | Vanney |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,297,143 B2 | 11/2007 | Woloszko et al. |
| 7,297,145 B2 | 11/2007 | Woloszko et al. |
| 7,311,708 B2 | 12/2007 | McClurken |
| 7,320,325 B2 | 1/2008 | Duchon et al. |
| 7,326,235 B2 | 2/2008 | Edwards |
| 7,331,957 B2 | 2/2008 | Woloszko et al. |
| 7,335,195 B2 | 2/2008 | Mehier |
| 7,347,859 B2 | 3/2008 | Garabedian et al. |
| 7,512,445 B2 | 3/2009 | Truckai et al. |
| 7,524,315 B2 | 4/2009 | Blott et al. |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,653,438 B2 | 1/2010 | Deem et al. |
| 7,717,909 B2 | 5/2010 | Strul et al. |
| 7,756,583 B2 | 7/2010 | Demarais et al. |

(56) References Cited

U.S. PATENT DOCUMENTS

| | | |
|---|---|---|
| 7,815,616 B2 | 10/2010 | Boehringer et al. |
| 7,815,646 B2 | 10/2010 | Hart |
| 7,846,160 B2 | 12/2010 | Payne et al. |
| 7,853,333 B2 | 12/2010 | Demarais |
| 7,873,417 B2 | 1/2011 | Demarais et al. |
| 7,937,143 B2 | 5/2011 | Demarais et al. |
| 7,993,323 B2 | 8/2011 | Barry et al. |
| 8,025,656 B2 | 9/2011 | Gruber et al. |
| 8,131,371 B2 | 3/2012 | Demarais et al. |
| 8,145,316 B2 | 3/2012 | Deem et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,192,424 B2 | 6/2012 | Woloszko |
| 8,197,470 B2 | 6/2012 | Sharkey et al. |
| 8,216,217 B2 | 7/2012 | Sharkey et al. |
| 8,221,401 B2 | 7/2012 | Sharkey et al. |
| 8,221,403 B2 | 7/2012 | Sharkey et al. |
| 8,226,645 B2 | 7/2012 | Harrington et al. |
| 8,313,485 B2 | 11/2012 | Shadduck |
| 8,343,078 B2 | 1/2013 | Toth |
| 8,394,037 B2 | 3/2013 | Toth |
| 8,486,060 B2 | 7/2013 | Kotmel et al. |
| 8,500,732 B2 | 8/2013 | Truckai et al. |
| 8,506,563 B2 | 8/2013 | Truckai et al. |
| 8,529,562 B2 | 9/2013 | Vissy et al. |
| 8,540,708 B2 | 9/2013 | Truckai et al. |
| 8,551,082 B2 | 10/2013 | Strul et al. |
| 8,574,226 B2 | 11/2013 | Shadduck |
| 8,579,888 B2 | 11/2013 | Hoey et al. |
| 8,579,892 B2 | 11/2013 | Hoey et al. |
| 8,585,645 B2 | 11/2013 | Barry et al. |
| 8,585,692 B2 | 11/2013 | Shadduck et al. |
| 8,597,289 B2 | 12/2013 | Layton, Jr. et al. |
| 8,647,349 B2 | 2/2014 | Gruber et al. |
| 8,690,873 B2 | 4/2014 | Truckai et al. |
| 8,715,278 B2 | 5/2014 | Toth et al. |
| 8,721,632 B2 | 5/2014 | Hoey et al. |
| 8,758,341 B2 | 6/2014 | Shadduck |
| 8,801,702 B2 | 8/2014 | Hoey et al. |
| 8,814,796 B2 | 8/2014 | Martin et al. |
| 8,840,625 B2 | 9/2014 | Adams et al. |
| 8,900,223 B2 | 12/2014 | Shadduck |
| 8,926,629 B2 | 1/2015 | Truckai |
| 8,936,592 B2 | 1/2015 | Beck et al. |
| 8,939,971 B2 | 1/2015 | Truckai et al. |
| 8,956,348 B2 | 2/2015 | Bek |
| 8,998,898 B2 | 4/2015 | Truckai et al. |
| 8,998,901 B2 | 4/2015 | Truckai et al. |
| 9,050,102 B2 | 6/2015 | Truckai |
| 9,050,103 B2 | 6/2015 | Truckai |
| 9,095,348 B2 | 8/2015 | Truckai et al. |
| 9,113,944 B2 | 8/2015 | Shadduck |
| 9,144,421 B1 | 9/2015 | Lau et al. |
| 9,186,208 B2 | 11/2015 | Truckai et al. |
| 9,204,889 B2 | 12/2015 | Shadduck |
| 9,242,122 B2 | 1/2016 | Tsoref et al. |
| 9,247,989 B2 | 2/2016 | Truckai |
| 9,259,262 B2 | 2/2016 | Hundertmark et al. |
| 9,277,952 B2 | 3/2016 | Burnett et al. |
| 9,283,022 B2 | 3/2016 | Burnett et al. |
| 9,289,257 B2 | 3/2016 | Toth et al. |
| 9,333,111 B2 | 5/2016 | Kochem et al. |
| 9,339,330 B2 | 5/2016 | Truckai |
| 9,408,657 B2 | 8/2016 | Burnett et al. |
| 9,421,059 B2 | 8/2016 | Truckai et al. |
| 9,427,556 B2 | 8/2016 | Burnett |
| 9,433,457 B2 | 9/2016 | Shadduck |
| 9,433,467 B2 | 9/2016 | Beck et al. |
| 9,486,267 B2 | 11/2016 | Burnett et al. |
| 9,498,274 B2 | 11/2016 | Burnett et al. |
| 9,554,853 B2 | 1/2017 | Strul et al. |
| 9,585,712 B2 | 3/2017 | Truckai |
| 9,615,875 B2 | 4/2017 | Shadduck |
| 9,636,171 B2 | 5/2017 | Toth et al. |
| 9,662,060 B2 | 5/2017 | Peliks et al. |
| 9,662,163 B2 | 5/2017 | Toth et al. |
| 9,743,974 B2 | 8/2017 | Gurskis et al. |
| 9,743,978 B2 | 8/2017 | Skalyni |
| 9,775,542 B2 | 10/2017 | Toth |
| 9,788,890 B2 | 10/2017 | Toth et al. |
| 9,814,520 B2 | 11/2017 | Truckai |
| 9,848,933 B2 | 12/2017 | Burnett et al. |
| 9,883,907 B2 | 2/2018 | Toth et al. |
| 9,895,192 B2 | 2/2018 | Model |
| 9,907,599 B2 | 3/2018 | Hoey et al. |
| 9,913,681 B2 | 3/2018 | Bueaudet |
| 9,943,353 B2 | 4/2018 | Hoey et al. |
| 9,993,290 B2 | 6/2018 | Chee et al. |
| 10,004,551 B2 | 6/2018 | Burnett et al. |
| 10,004,553 B2 | 7/2018 | Churchill et al. |
| 10,052,150 B2 | 8/2018 | Truckai et al. |
| 10,105,176 B2 | 10/2018 | Toth et al. |
| 10,154,871 B2 | 12/2018 | Sharkey et al. |
| 10,179,019 B2 | 1/2019 | Chee et al. |
| 10,213,151 B2 | 2/2019 | Filloux et al. |
| 10,213,335 B2 | 2/2019 | Burnett et al. |
| 10,238,446 B2 | 3/2019 | Gurskis et al. |
| 10,299,856 B2 | 5/2019 | Chee et al. |
| 10,456,194 B2 | 10/2019 | Truckai |
| 10,499,981 B2 | 12/2019 | Model |
| 10,524,847 B2 | 1/2020 | Shadduck |
| 10,548,653 B2 | 2/2020 | Hoey et al. |
| 10,575,898 B2 | 3/2020 | Chee et al. |
| 10,588,689 B2 | 3/2020 | Truckai |
| 10,617,461 B2 | 4/2020 | Toth et al. |
| 10,624,694 B2 | 4/2020 | Kochem et al. |
| 10,722,298 B2 | 7/2020 | Skalnyi |
| 10,758,300 B2 | 9/2020 | Truckai et al. |
| 10,779,877 B2 | 9/2020 | Churchill et al. |
| 2002/0007180 A1 | 1/2002 | Wittenberger et al. |
| 2002/0013601 A1 | 1/2002 | Nobles et al. |
| 2002/0019627 A1 | 2/2002 | Maguire et al. |
| 2002/0077516 A1 | 6/2002 | Flanigan |
| 2002/0078956 A1 | 6/2002 | Sharpe et al. |
| 2002/0111386 A1 | 8/2002 | Sekins et al. |
| 2002/0128638 A1 | 9/2002 | Chauvet et al. |
| 2002/0133147 A1 | 9/2002 | Marchitto et al. |
| 2002/0151917 A1 | 10/2002 | Barry |
| 2002/0161326 A1 | 10/2002 | Sussman et al. |
| 2002/0173815 A1 | 11/2002 | Hogendijk et al. |
| 2002/0177846 A1 | 11/2002 | Muller et al. |
| 2003/0028189 A1 | 2/2003 | Woloszko et al. |
| 2003/0097126 A1 | 5/2003 | Woloszko et al. |
| 2003/0099279 A1 | 5/2003 | Venkatasubramanian et al. |
| 2003/0130738 A1 | 7/2003 | Hovda et al. |
| 2003/0144654 A1 | 7/2003 | Hilal |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0217962 A1 | 11/2003 | Childers et al. |
| 2003/0220604 A1 | 11/2003 | Al-Anazi |
| 2003/0225364 A1 | 12/2003 | Kraft et al. |
| 2004/0002698 A1 | 1/2004 | Hua Xiao et al. |
| 2004/0024399 A1 | 2/2004 | Sharps et al. |
| 2004/0047855 A1 | 3/2004 | Ingenito |
| 2004/0049180 A1 | 3/2004 | Sharps et al. |
| 2004/0055606 A1 | 3/2004 | Hendricksen et al. |
| 2004/0068306 A1 | 4/2004 | Shadduck |
| 2004/0116922 A1 | 6/2004 | Hovda et al. |
| 2004/0199226 A1 | 10/2004 | Shadduck |
| 2004/0230190 A1 | 11/2004 | Dahla et al. |
| 2005/0010205 A1 | 1/2005 | Hovda et al. |
| 2005/0119650 A1 | 6/2005 | Sanders et al. |
| 2005/0143728 A1 | 6/2005 | Sampson et al. |
| 2005/0166925 A1 | 8/2005 | Wilson et al. |
| 2005/0171574 A1 | 8/2005 | Rubinsky et al. |
| 2005/0171582 A1 | 8/2005 | Matlock |
| 2005/0177147 A1 | 8/2005 | Vancelette et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |

(56) References Cited

U.S. PATENT DOCUMENTS

| | | |
|---|---|---|
| 2005/0228424 A1 | 10/2005 | Khashayar et al. |
| 2005/0240171 A1 | 10/2005 | Forrest |
| 2005/0240239 A1 | 10/2005 | Boveja et al. |
| 2005/0267467 A1 | 12/2005 | Paul et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0058831 A1 | 3/2006 | Atad |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161147 A1 | 7/2006 | Privitera et al. |
| 2006/0161233 A1 | 7/2006 | Barry et al. |
| 2006/0200076 A1 | 9/2006 | Gonzalez et al. |
| 2006/0206150 A1 | 9/2006 | Demarais et al. |
| 2006/0224154 A1 | 10/2006 | Shadduck et al. |
| 2006/0265053 A1 | 11/2006 | Hunt |
| 2006/0271111 A1 | 11/2006 | Demarais et al. |
| 2007/0021713 A1 | 1/2007 | Kumar et al. |
| 2007/0032785 A1 | 2/2007 | Diederich et al. |
| 2007/0066990 A1 | 3/2007 | Marsella et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0225744 A1 | 9/2007 | Nobles et al. |
| 2007/0239197 A1 | 10/2007 | Dubey et al. |
| 2007/0288051 A1 | 12/2007 | Beyer et al. |
| 2008/0033493 A1 | 2/2008 | Deckman et al. |
| 2008/0077201 A1 | 3/2008 | Levinson et al. |
| 2008/0125747 A1 | 5/2008 | Prokop |
| 2008/0132826 A1 | 6/2008 | Shadduck et al. |
| 2008/0135053 A1 | 6/2008 | Gruber et al. |
| 2008/0161788 A1 | 7/2008 | Dando et al. |
| 2008/0167664 A1 | 7/2008 | Payne et al. |
| 2008/0249467 A1 | 10/2008 | Burnett et al. |
| 2009/0024108 A1 | 1/2009 | Lee-Sepsick et al. |
| 2009/0030412 A1 | 1/2009 | Willis et al. |
| 2009/0076409 A1 | 3/2009 | Wu et al. |
| 2009/0125010 A1 | 5/2009 | Sharkey et al. |
| 2009/0216220 A1 | 8/2009 | Hoey et al. |
| 2009/0306640 A1 | 12/2009 | Glaze et al. |
| 2010/0078046 A1 | 4/2010 | Labib et al. |
| 2010/0082021 A1 | 4/2010 | Gutierrez et al. |
| 2010/0094268 A1 | 4/2010 | Bouthillier et al. |
| 2010/0094270 A1 | 4/2010 | Sharma |
| 2010/0100091 A1 | 4/2010 | Truckai |
| 2010/0100094 A1 | 4/2010 | Truckai |
| 2010/0106152 A1 | 4/2010 | Truckai et al. |
| 2010/0114083 A1 | 5/2010 | Sharma |
| 2010/0114089 A1 | 5/2010 | Truckai et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |
| 2010/0204688 A1 | 8/2010 | Hoey et al. |
| 2010/0228222 A1 | 9/2010 | Williams et al. |
| 2010/0249773 A1 | 9/2010 | Clark et al. |
| 2010/0262133 A1 | 10/2010 | Hoey et al. |
| 2011/0009829 A1 | 1/2011 | Kosinski et al. |
| 2011/0054508 A1 | 3/2011 | Zhou et al. |
| 2011/0077628 A1 | 3/2011 | Hoey et al. |
| 2011/0112400 A1 | 5/2011 | Emery et al. |
| 2011/0112432 A1 | 5/2011 | Toth |
| 2011/0112433 A1 | 5/2011 | Toth |
| 2011/0112523 A1 | 5/2011 | Toth et al. |
| 2011/0118718 A1 | 5/2011 | Toth et al. |
| 2011/0118719 A1 | 5/2011 | Vissy et al. |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0208096 A1 | 8/2011 | Demarais et al. |
| 2011/0208178 A1 | 8/2011 | Truckai |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136343 A1 | 5/2012 | Burnett |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0197198 A1 | 8/2012 | Demarais et al. |
| 2012/0197245 A1 | 8/2012 | Burnett et al. |
| 2012/0209281 A1 | 8/2012 | Truckai |
| 2012/0232545 A1 | 9/2012 | Truckai et al. |
| 2012/0245583 A1 | 9/2012 | Truckai et al. |
| 2012/0259271 A1 | 10/2012 | Shadduck et al. |
| 2013/0006231 A1 | 1/2013 | Sharma et al. |
| 2013/0116683 A1 | 5/2013 | Shadduck et al. |
| 2013/0237978 A1 | 9/2013 | Shadduck et al. |
| 2013/0261539 A1 | 10/2013 | King |
| 2013/0296837 A1 | 11/2013 | Burnett et al. |
| 2014/0031805 A1 | 1/2014 | Shadduck |
| 2014/0088575 A1 | 3/2014 | Loeb |
| 2014/0088581 A1 | 3/2014 | Kelly et al. |
| 2014/0200570 A1 | 7/2014 | Hoey et al. |
| 2014/0236129 A1 | 8/2014 | Radi et al. |
| 2015/0025515 A1 | 1/2015 | Hoey et al. |
| 2015/0119795 A1 | 4/2015 | Germain et al. |
| 2015/0334079 A1 | 11/2015 | Laidlaw et al. |
| 2017/0258511 A1 | 9/2017 | Peliks et al. |
| 2017/0354452 A1 | 12/2017 | Gurskis et al. |
| 2018/0168713 A1 | 6/2018 | Hoey et al. |
| 2018/0193079 A1 | 7/2018 | Hoey et al. |
| 2018/0199982 A1 | 7/2018 | Hoey et al. |
| 2018/0289416 A1 | 10/2018 | Chee et al. |
| 2019/0038210 A1 | 2/2019 | Peliks et al. |
| 2019/0216523 A1 | 7/2019 | Gurskis et al. |
| 2019/0223934 A1 | 7/2019 | Shadduck |
| 2020/0188008 A1 | 6/2020 | Hoey et al. |
| 2020/0197081 A1 | 6/2020 | Chee et al. |

FOREIGN PATENT DOCUMENTS

| | | |
|---|---|---|
| CN | 102271602 A | 12/2011 |
| CN | 103717126 A | 4/2014 |
| CN | 104135960 A | 11/2014 |
| JP | H06-285074 A | 10/1994 |
| JP | 2000502585 A | 3/2000 |
| JP | 20003513742 A | 4/2003 |
| JP | 2010516351 A | 5/2010 |
| WO | WO98/57603 A1 | 12/1998 |
| WO | WO99/53853 A1 | 10/1999 |
| WO | WO00/011927 A2 | 3/2000 |
| WO | WO00/29055 A1 | 5/2000 |
| WO | WO01/85012 A2 | 11/2001 |
| WO | WO02/069821 A1 | 9/2002 |
| WO | WO 03/070302 A1 | 8/2003 |
| WO | WO2005/025635 A2 | 3/2005 |
| WO | WO2005/102175 A2 | 11/2005 |
| WO | WO2006/003665 A2 | 1/2006 |
| WO | WO 2006/055695 A1 | 5/2006 |
| WO | WO2006/108974 A1 | 10/2006 |
| WO | WO2009/009398 A1 | 1/2009 |
| WO | WO2010/045055 A2 | 4/2010 |
| WO | WO2010/048007 A1 | 4/2010 |
| WO | WO2011/025658 A1 | 3/2011 |
| WO | WO2011/053599 A1 | 5/2011 |

(56) References Cited

FOREIGN PATENT DOCUMENTS

| WO | WO2011/060189 A1 | 5/2011 |
|----|------------------|--------|
| WO | WO2011/060191 A1 | 5/2011 |
| WO | WO2012/106260 A2 | 8/2012 |

OTHER PUBLICATIONS

Blacker; Vaporization of the uterus; J. Obstet. & Gyn.; vol. 1; Issue 5; pp. 488-511; May 1902.

Fishman et. al.; A randomized trial comparing lung-volume-reduction surgery with medical therapy for severe emphysema; N Engl J Med; 348(210. pp. 2059-2073; May 22, 2003.

Homasson et. al.; Bronchoscopic cryotherapy for airway strictures caused by tumors; Chest; 90(2); pp. 159-164; Aug. 1, 1986.

Marasso et al.; Radiofrequency resection of bronchial tumours in combination with cryotherapy: evaluation of a new technique; Thorax; 53(2); pp. 106-109; Feb. 1998.

Marasso et. al.; Cryosurgery in bronchoscopic treatment of tracheobronchial stenosis; Cheat; 103(2); pp. 472-474; Feb. 1993.

Morice et. al.; Endobronchial argon plasma coagulation for treatment of hemoptysis and neoplastic airway obstruction; Chest; 119(3); pp. 781-787; Mar. 1, 2001.

Neuwirth et al.; The endometrial ablator; a new instrument; Obst. & Gyn.; vol. 83; No. 5; part 1; pp. 792-796; May 1994.

Prior et al.; Treatment of mennorrhagia by radiofrequency heating; Int. J. Hyperthermia; vol. 7; No. 2; pp. 213-220; Mar.-Apr. 1991.

Tschirren et. al.; Intrathoracic airway trees: segmentation and airway morphology analysis from low-dose CT scans; IEEE Transactions on Medical Imaging; 24(12); pp. 1529-1539; Dec. 2005.

Unger et. al.; Monolithic Microfabricated Valves and Pumps by Multilayer Soft Lithography; Science, 288(5463); pp. 113-116; Apr. 7, 2000.

Van De Velde; Vapo-cauterization of the uterus; Amer. J. Med. Sci.; vol. CXVIII (118); Nov. 1899.

Sharkey et al.; U.S. Appl. No. 16/224,287 entitled "Uterine therapy device and method," filed Dec. 18, 2018.

Sharkey et al.; U.S. Appl. No. 16/224,363 entitled "Uterine therapy device and method," filed Dec. 18, 2018.

Kim et al.; Polyurethanes having shape memory effect; Polymer-Letchworth; 37(26); pp. 5781-5793; Jan. 1996.

Poco; Industry news: Poco introduces improved CXT-CXT-xtra; 2 pages; retrieved from the internet (https://web.archive.org/web/20061215223908/http://www.poco.com/us/) on Feb. 2020.

Stanford; Capacitor micro machined ultrasonic transducer (cMUT); 10 pages; retrieved from the Internet (https://web.archive.org/web/20040205083311/http://acoustics.stanford.edu/group/cmut1.pdf) on Feb. 20, 2020.

Chee et al.; U.S. Appl. No. 16/422,835 entitled "Systems and methods for performing endometrial ablation," filed May 24, 2019.

INTEGRITY TESTING METHOD AND APPARATUS FOR DELIVERING VAPOR TO THE UTERUS

CROSS REFERENCE TO RELATED APPLICATIONS

This application is a division of U.S. application Ser. No. 14/719,037, filed May 21, 2015, titled "Integrity Testing Method and Apparatus for Delivering Vapor to the Uterus", now U.S. Pat. No. 10,179,019; which claims the benefit of U.S. Provisional Application No. 62/002,070, filed May 22, 2014, titled "Integrity Testing Method and Apparatus for Delivering Vapor to the Uterus", each of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure generally relates to uterine procedures incorporating a distension media such as a fluid or a gas that could be used with endoscopic procedures or other visualization systems such ultrasound or fluoroscopy. The present disclosure is particular suited for endometrial ablation of the uterine lining. More specifically, the present disclosure relates to endometrial ablation with a heated vapor.

BACKGROUND

Endometrial ablation (i.e., the removal or destruction of the endometrial lining of the uterus) is used as an alternative to hysterectomy for treating menorrhagia, or other uterine diseases. One prior technique for performing endometrial ablation employs a resectoscope (i.e., a hysteroscope with a built-in wire loop or other ablative devices) that is inserted transcervically into the uterus, and uses radio-frequency electrical current (RF current) to remove or coagulate the endometrial tissue. These standard techniques typically are performed in a hospital setting and importantly utilize hysteroscopy for visualization of the procedure while treating the uterine lining.

Some approaches make use of heated fluid to ablate the endometrium. For example, early journal articles describe the use of steam to treat uterine hemorrhage. The use of steam for this purpose was later discredited, apparently due to patient morbidity and mortality. See, e.g., Fuller U.S. Pat. No. 6,139,571. More recent descriptions of the use of injecting hot fluid into the uterus have been described. Uterine therapies employing a contained fluid have also been described.

In an effort to simplify the procedure, approaches have been developed that do not require concurrent hysteroscopic visualization. In practice, many of these techniques recommend that the physician or user employ hysteroscopy to visualize and inspect the uterine cavity prior to performing the endometrial ablation procedure. In addition, hysteroscopy may be employed at the conclusion of the endometrial ablation procedure as a method to inspect the uterine cavity post treatment. During this hysteroscopic inspection, the physician is verifying that the uterine cavity is not perforated although perforations may not be readily apparent even with hysteroscopic visualization. In general, a physician seeks to avoid perforations for many reasons including the potential for unintended injuries to neighboring organs and maintaining or confining the treatment area to specifically the uterine cavity in the case of endometrial ablation procedures.

Endometrial ablation techniques that do not require active hysteroscopic visualization during treatment operation are commonly referred to as "blind" techniques since the physician is using tactile feel, or markers and indicia on the endometrial ablation device to indicate proper placement of the device in the uterine cavity. One of these particular devices utilizes a balloon-based system using heated saline as the thermal energy source for the ablation of tissue. High frequency, or radiofrequency (RF), energy has also been used to perform thermal ablation of endometrial tissue. Current products for performing endometrial ablation include the NOVASURE® procedure and a system marketed under the trade name THERMACHOICE®, by Ethicon, Inc. of Somerville, N.J. Cryogenic ablation, or "cryoablation," such as HER OPTION® from American Medical Systems, Inc., is another endometrial treatment approach. All of the products above are characterized as "blind" or not requiring direct hysteroscopic visualization during the treatment.

In utilizing an endometrial ablation technology that does not require hysteroscopic visualization, it would be beneficial to employ a test to verify that the uterine cavity is intact or unperforated prior to performing the treatment. Such tests are referred to as uterine integrity tests and these tests can be performed with endometrial ablation procedures and any procedure of the uterus or hollow body cavity or organ. In addition, these tests can be used with hysteroscopic procedures since a perforation may not be readily detected even under direct vision.

Integrity tests employ saline or gas, preferably carbon dioxide gas, as agents to verify if the uterine cavity is intact in regards to holding fluid or gas pressure. The gas or fluid is supplied under pressure to the uterine cavity and a leak in the uterine cavity, whether it is a perforation, an unsealed cervical canal, or the effect of excess fluid exiting the fallopian tubes, can be discerned. Stern et al. (U.S. Pat. No. 5,562,720) and Sampson et al. (U.S. Pat. Nos. 6,554,780, 6,743,184, 6,872,183, and 7,063,670) describe such pressure techniques while other approaches check for fluid imbalances between an input source and output collection using volume measurements. Other approaches mention using flow rate and pressure measurements.

SUMMARY

A method of performing a patency test for a uterine ablation device is provided, comprising inserting the uterine ablation device into a uterus of a patient, inflating an outflow valve to seal an outflow lumen of the uterine ablation device, delivering gas or fluid from an inflow lumen of the uterine ablation device into the uterus, partially deflating the outflow valve to remove gas or fluid from the uterus with the outflow lumen of the uterine ablation device, and determining that the uterine ablation device is not clogged or embedded in tissue if a flow rate of gas or fluid is observed above a threshold value in the outflow lumen of the uterine ablation device.

In some embodiments, the partially deflating step further comprises pulsing the deflating of the outflow valve at a specified duty cycle until flow of gas or fluid through the outflow lumen begins.

In one embodiment, the partially deflating step further comprises pulsing the deflating of the outflow valve a specified duty cycle until a uterine pressure decreases.

In yet another embodiment, the partially deflating step further comprises pulsing the deflating of the outflow valve at a high duty cycle, then pulsing the deflating of the outflow valve at a lower duty cycle when flow of gas or fluid through the outflow lumen begins.

A method of performing a patency test for a uterine ablation device is provided, comprising inserting the uterine ablation device into a uterus of a patient, closing an outflow valve to seal an outflow lumen of the uterine ablation device, delivering gas or fluid from an inflow lumen of the uterine ablation device into the uterus, partially opening the outflow valve to remove gas or fluid from the uterus with the outflow lumen of the uterine ablation device, and determining that the uterine ablation device is not clogged or embedded in tissue if a flow rate of gas or fluid is observed above a threshold value in the outflow lumen of the uterine ablation device.

In some embodiments, the partially deflating step further comprises pulsing the deflating of the outflow valve at a specified duty cycle until flow of gas or fluid through the outflow lumen begins.

In one embodiment, the partially deflating step further comprises pulsing the deflating of the outflow valve a specified duty cycle until a uterine pressure decreases.

In yet another embodiment, the partially deflating step further comprises pulsing the deflating of the outflow valve at a high duty cycle, then pulsing the deflating of the outflow valve at a lower duty cycle when flow of gas or fluid through the outflow lumen begins.

A uterine ablation device is provided, comprising a shafted adapted to be inserted into a uterus of a patient, the shaft including an inflow outflow lumen and an inflow lumen, a gas/fluid source configured to deliver gas or fluid through the inflow lumen of the shaft into the uterus, an outflow valve configured to seal the outflow lumen of the shaft, a flow meter disposed in or near the outflow lumen and configured to measure a flow rate of gas or fluid in the outflow lumen, and an electronic controller operatively coupled to the gas/fluid source, the outflow valve, and the flow meter, the electronic controller being configured to partially open the outflow valve to remove gas or fluid from the uterus through the outflow lumen of the uterine ablation device and determine that the uterine ablation device is not clogged or embedded in tissue if a flow rate of gas or fluid measured by the flow meter is above a threshold value.

In some embodiments, the threshold value is 5 ml/min.

In another embodiment, the electronic controller is configured to determine that the uterine ablation device is not clogged or embedded in tissue if the flow rate of gas or fluid measured by the flow meter is above the threshold value during a rolling patency test time window. In some embodiments, the patency test time window is a 5 second time period.

A method of performing a uterine integrity test is provided, comprising inserting a uterine device into the uterus of the patient, delivering gas or fluid from an inflow lumen of the uterine device into the uterus, measuring a flow rate of the gas or fluid during a rolling time window as it is delivered into the uterus, calculating a delta flow value from a minimum flow rate and a maximum flow of the gas or fluid during the rolling time window, and determining that the uterus is sealed if the flow rate decreases below a flow rate threshold value, and if the delta flow value is below the flow rate threshold value.

In some embodiments, the flow rate threshold value comprises 5 ml/min.

In another embodiment, the rolling time window comprises 15 seconds.

DETAILED DESCRIPTION

Figure 1A:
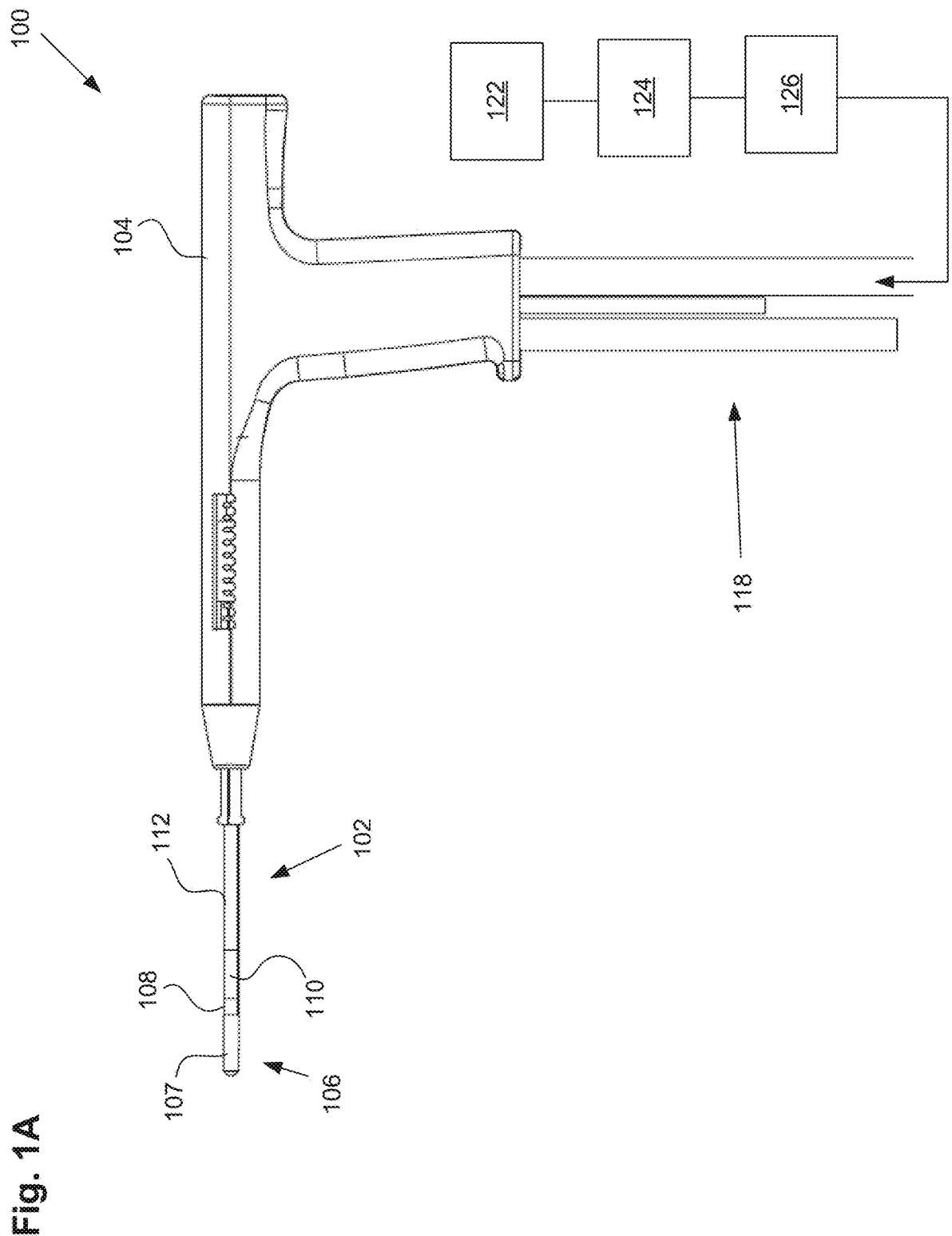
FIGS. 1A-1B illustrate one embodiment of a uterine ablation device.

FIG. 1A illustrates a uterine ablation device 100 sized and configured to access the endometrium of a uterus and to deliver a heated vapor to the uterus to ablate uterine tissue. The device can be configured to ablate and treat the endometrial lining of the uterus as an alternative to hysterectomy for treating menorrhagia or other uterine diseases. In some embodiments, the device 100 can be configured to gain access to the uterus by being inserted through a cannula or hysteroscope. The device 100 can include shaft 102, handle 104, distal tip 106, vapor ports 107, distal anchor or distal balloon 108, central or sealing balloon 110, proximal or positioning balloon 112, and connection lumens 118, which can couple the uterine ablation device to a control system (not shown) comprising a computer, a vapor generation system, and mechanisms configured to inflate and deflate the balloons as well as control the delivery and removal of integrity gas/fluid and vapor from the device. Additionally, connection lumens 118 can connect device 100 to a gas/fluid source 122, pressure regulator 124, and flow meter(s) 126. Vapor ports 107 near the distal tip 106 of the device can be fluidly coupled to the connection lumens 118 via inflow and outflow lumens (not shown). The vapor ports, inflow and outflow lumens, connection lumens, gas/fluid source, pressure regulator, and flow meters can be configured for testing the integrity of the patient's uterus, proper placement of the device, and verifying the presence of flow between the inflow and outflow lumens of the device.

The flow meter can be any flow meter as known in the art, including a thermal mass flow meter, an ultrasonic flow meter, a paddlewheel, or a variable area flow meter. In one embodiment, an ultrasonic flow meter that utilizes transit time and Doppler flow readings is advantageous since it is a non-contact system that does not need to physically interact with the fluid or gas media being employed in the integrity test. An ultrasonic flow meter can be easily adaptable to the exterior dimensions of an inflow lumen. In addition, a drip chamber within the inflow lumen can be used to manually visualize or record drips or flow from the fluid source as the integrity test indicates a sealed uterine cavity. In some uterine procedures, it may be advantageous to use other types of fluid besides saline including Lactated Ringers, non-isotonic solutions for certain electrosurgical procedures, gels, foams, fluids of varying viscosity for some ultrasonographic procedures, or other fluids used in uterine procedures.

In one embodiment, a one way valve can be placed in the inflow lumen on either side of the flow meter relative to the gas/fluid source. The one way valve can allow for the flow of gas/fluid (e.g., saline) from the gas/fluid source to the device and uterine cavity. The one way valve should not interfere with the operation of the flow meter and its readings. In operation, the uterine cavity is a muscle that can undergo significant contractions during the integrity and patency tests. These contractions can push the fluid retrograde back through the saline lumen and past the flow meter. In doing so, flow meter measurements can become difficult to interpret or may produce sinusoidal waves in the output readings. The placement of the one way valve in the inflow lumen can eliminate retrograde fluid flow and stabilize readings for the flow meter during episodes of uterine contractions.

Handle 104 can be an ergonomic handle and can include features and controls for using the device (e.g., buttons, levers, indicia for providing feedback for depths of insertion, valves, etc.), including features for controlling inflation of balloons 108, 110, and 112, and for controlling the delivery and removal of integrity test gas/fluid and heated vapor from the device. The handle can also include features and controls for testing the integrity of the patient's uterus, proper placement of the device and verifying the presence of flow between the inflow and outflow lumens of the device.

The balloons described herein can be any type of flexible balloon, such as rubber, latex, urethane, silicone, PET, LDPE, parylene, nylon, PE, combinations of these polymers, or can be manufactured from any other suitable material as known in the art. It should be noted that in some embodiments, the distal anchor comprises a balloon, but in other embodiments, the distal anchor comprises an expandable anchor or expansion mechanism, such as expandable frames, filters, nets, or cages, or non-expandable components that increase the diameter of the shaft of the uterine ablation device. For purposes of this disclosure, however, the distal anchor may be referred to as a distal anchor or as a distal balloon.

Shaft 102 can be configured to deliver a heated vapor from a remote boiler (not shown) through the device and out of vapor ports 107 in distal tip 106. The shaft can also be configured to return vapor that has exited the device, including bodily fluids, uterine materials, and condensate back through the vapor ports and into the shaft. In FIG. 1A, vapor ports 107 are illustrated as including both the vapor delivery and vapor return ports. However, in other embodiments, the vapor delivery ports can be separate and distinct from the vapor return ports. For example, vapor delivery ports are intended to provide an even distribution of heated vapor through a cavity, and may comprise small lumens or holes on the end of the shaft. The vapor return ports, in contrast, are intended to return used vapor and condensate, and may comprise larger slots to prevent blood, tissue, etc. from blocking or clogging the return lumen. The device comprises inflow and outflow gas and/or fluid delivery channels to conduct uterine integrity and patency tests. In some embodiments, the lumens to deliver and return vapor are the same as the channels to deliver and return gas and/or fluid for the uterine integrity and patency tests.

Referring still to FIG. 1A, uterine ablation device 100 is shown in a collapsed delivery configuration, with distal balloon 108, sealing balloon 110, and positioning balloon 112 deflated to reduce the cross sectional diameter of the device and can be 6 mm in diameter during insertion or smaller. When the device is in the delivery configuration, the reduced profile allows for easier access to through the vagina, cervical canal, and cervix to gain access to the uterus, and provides reduced patient discomfort during insertion. In some embodiments, the outer dimensions of the uterine ablation device are such that introduction of the device into the uterine cavity can be achieved without the need for mechanical or pharmacological dilation of the os prior to device introduction.

Figure 1B:
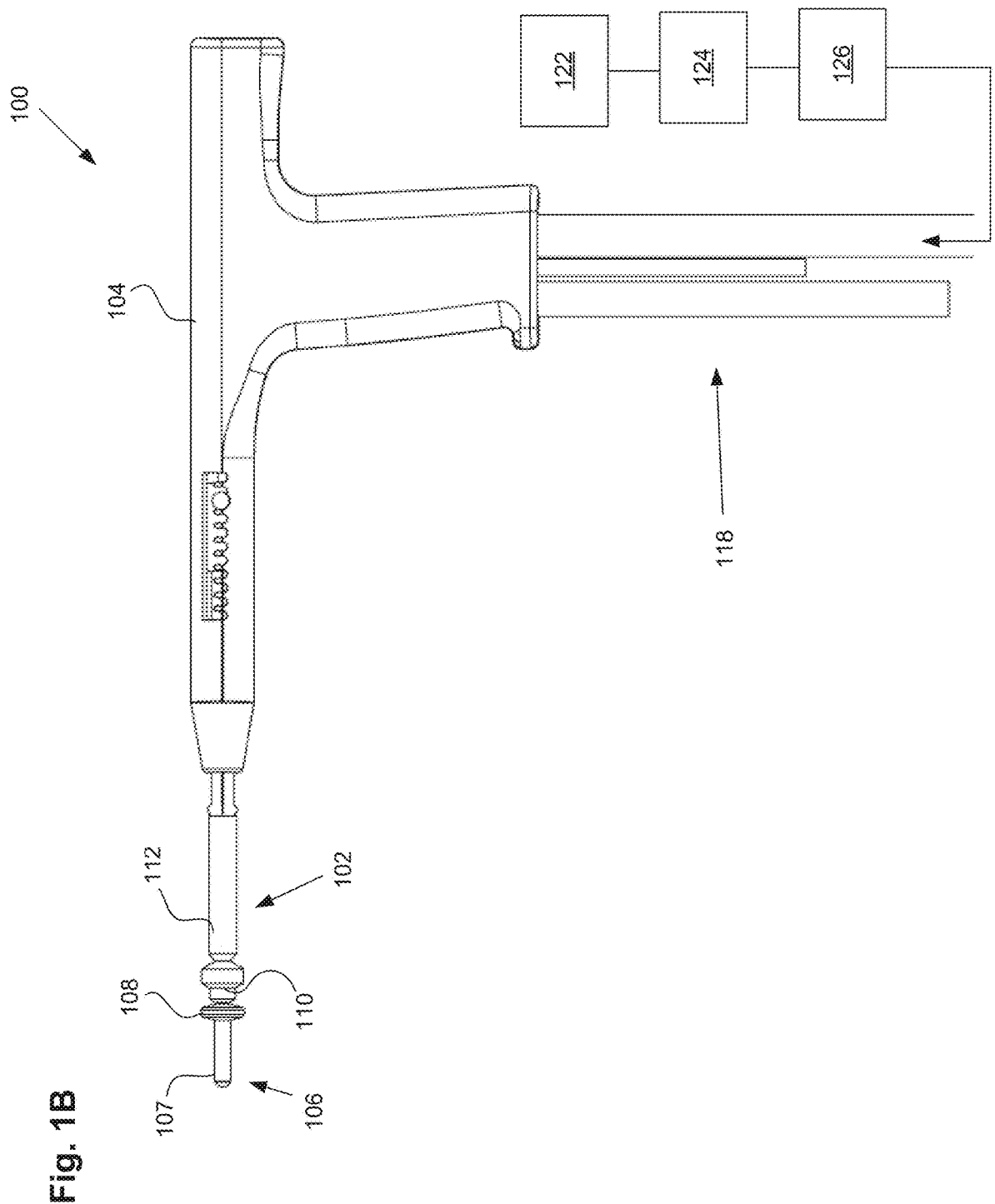

FIG. 1B illustrates the uterine ablation device 100 of FIG. 1A with all three balloons inflated, including distal balloon 108, central sealing balloon 110, and positioning balloon 112. The central balloon can be inflated with a fluid, such as saline, or alternatively, can be inflated with air. Although three balloons are depicted in FIG. 1B, in other variations one, two, four, or more balloons may be provided, and other balloon shapes may be used. The positioning balloon can be inflated with a room temperature medium, a cooled medium, or alternatively, a heated medium. In some embodiments, the central sealing balloon comprises a length along shaft 102 of approximately 15 mm to 25 mm. The central balloon can be disposed on the shaft between the distal balloon or anchor and the proximal balloon. In some embodiments, the central balloon is adjacent to both the distal balloon and the proximal balloon. In other embodiments, there is a small gap or space between one or more of the balloons. The length and position of the central balloon on the shaft ensures that when inflated, the central balloon seals the cervix off from the uterus near the internal os, but the balloon does not extend into the uterus or into the vagina of the patient. The central and proximal balloons can comprise any diameter, but preferably should have a diameter large enough to be able to engage the walls of the cervix and/or the vagina in the average female patient. For instance, the central balloon may have an inflated outer diameter of 10 mm and accommodate 9.5 psi of pressure in actual use. The proximal balloon can have a larger diameter, such as 17 mm and a lower inflation pressure of 7 psi.

Placement of the ablation device of FIGS. 1A-1B will now be described. The distal tip of the ablation device can be inserted past an external os into the cervical canal of the patient, and past an internal os of the patient to gain access to the uterus. In one embodiment, the distal balloon can be positioned within the uterus distal to the internal os, the sealing balloon can be positioned at or proximal to the internal os and extending into the cervical canal, and the positioning balloon can be positioned within the cervical canal and extending proximally into or towards the vagina.

Once the distal tip of the ablation device is disposed within the uterus, just distal to the internal os, the distal balloon can be inflated to the desired pressure. In some embodiments, the balloon can be inflated to a pressure of up to approximately 20 to 30 psi so as to prevent accidental withdrawal of the ablation device from the uterus. It should be noted that at this point, the distal balloon is positioned slightly past the internal os of the cervix. Inflation of the distal balloon can later serve as an anchor to prevent the device from sliding proximally out of the uterus.

Figure 2:
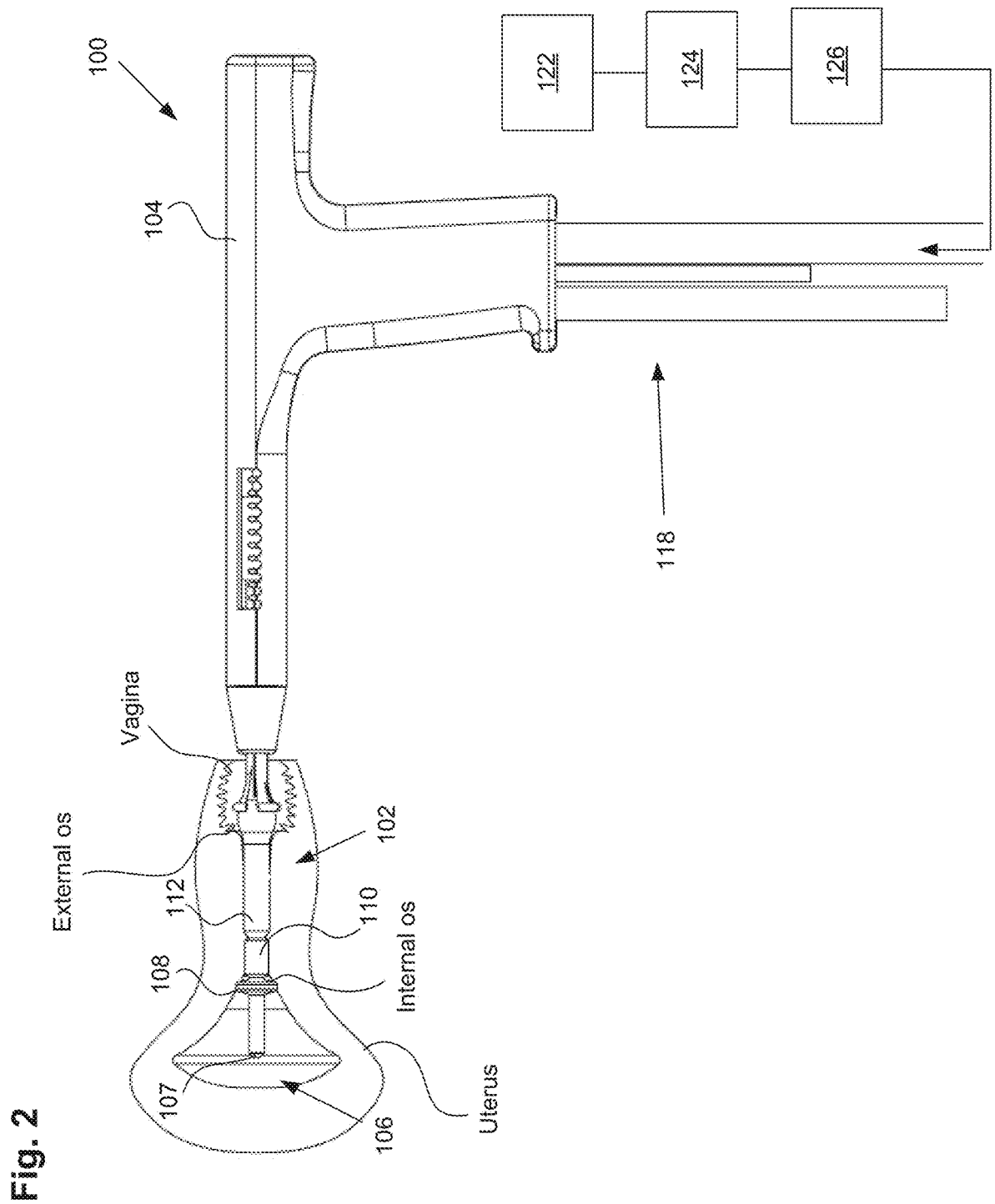
FIG. 2 shows an embodiment of a uterine ablation device inserted into a uterus.

After inflating the distal balloon, the proximal balloon can be inflated to cause the device to assume a positioned configuration, with the distal balloon fully seated against the internal os and the positioning or proximal balloon expanded within the cervix and extending past the external os into the vagina. As the proximal balloon is inflated, the balloon can expand outwardly from the cervix into the relatively unconstrained space of the vagina, which creates a compression force that pulls the device and the distal balloon proximally to engage against the interior portion of the internal os (also known as the cervical ostium or cervical os). FIG. 2 illustrates ablation device 100 inserted into the uterus of a patient with balloons 108, 110, and 112 inflated as described above.

After positioning the ablation device but prior to delivery of vapor, it can be advantageous to assess the integrity of the uterus to test that the vapor delivery tip of the device is positioned within a sealed uterus and to test that there is flow between the inflow and outflow lumens, by performing an integrity test and a patency test. The amount of fluid and rate in which it flows into the uterine cavity can provide the physician an indication of the size of the uterine cavity and whether the device is in a false passage. An integrity test can assess that the uterus is sealed, and determine leaks originating from 1) perforations to the uterine wall, or 2) leaks from inadequate sealing at the cervix or 3) leaks from the fallopian tubes.

A second test that made an assessment for patency, referred to as the device lumens patency test or patency test, could provide an indication to the physician whether the device was clogged with debris or placed within a false passage. This additional information to the physician, in conjunction with the integrity test, can provide greater assurance to the physician of device location during "blind" endometrial ablation procedures.

In clinical use, a uterine integrity and patency test could be useful for additional uterine procedures besides uterine ablation procedures such as the implantation of a device, implant, or a diagnostic or therapeutic agent. In these cases, a separate unit or module that can conduct a uterine integrity and patency test, sequentially, separately, or individually, with a separate uterine cavity introducer can be employed without a uterine ablation device or system.

In one embodiment, a uterine integrity test can contain the following elements and steps. Referring to FIGS. 1A-1B and FIG. 2, gas/fluid source 122 can be connected to pressure regulator 124 comprising either one regulator or an additional back pressure regulator. The gas/fluid source can contain a gas, such as $CO_2$, or inert gases, or a fluid, such as saline, Ringer's Lactate, non-isotonic solutions, glycerine, and mineral oil for example. The regulator 124 can be configured to keep the pressure of the external gas source below a safety threshold value. In one embodiment, the safety threshold value can be approximately 70 mm Hg. The actual pressure amount or graduation may not be monitored and may not need to be. The fluid or gas from gas/fluid source 122 can be driven at a constant pressure bounded by the safety threshold value (e.g., can be bounded by the maximum pressure the uterus will see during treatment, such as 70 mm Hg). In addition, it can be useful to operate a uterine integrity test at a pressure equal to higher than the pressure required for conducting the endometrial ablation or other uterine procedure.

In one embodiment, gas/fluid pressure can be achieved by elevating the gas/fluid source 122 a height distance above the uterine cavity to create pressure. This height elevation can be verified by a measuring stick, tape or laser. An example of a clinically used height for a saline bag would be at least 30 inches above the patient's uterus. At this height, the pressure would be between 50 and 70 mmHg. This pressure is low enough to be below the reported opening pressure of the fallopian tubes. In addition, a pressure sensor within the uterine cavity can verify that the appropriate amount of pressure is being applied for the integrity test and patency tests. A self-adjusting feedback mechanism can be employed to raise or lower the pressure of the saline source in response to pressure measurements taken from within the uterine cavity. As an example, this feedback mechanism can raise or lower the height of the saline source in response to the pressure measurements taken from within the uterine cavity.

In some embodiments, the system can measure a flow rate of gas/fluid exiting the distal lumen of the uterine device or uterine ablation device during the uterine integrity test. This flow rate can also be used to determine the proper pressure or height of the gas/fluid source. For instance, flow rate readings can be taken while the gas/fluid source is at a certain height and the uterine device maintained within a known condition or in free space. As the height of the gas/fluid source is raised or lowered, the flow rate of the gas/fluid will respond accordingly until the gas/fluid source is placed at a height at the desired flow rate, or is pressurized to the desired amount Likewise, the gas/fluid source can be raised or lowered by a self-adjusting feedback mechanism in response to the measured flow rate.

In some embodiments, the uterine ablation device can further include a flow meter 126 having a read out mechanism (not shown) to the end user. In one embodiment, the flow meter can comprise an ultrasound sensor, or an optical sensor configured to sense the drip rate of the gas/fluid. In some embodiments, the flow meter can be disposed near distal tip 106 of the device. In other embodiments, the flow meter can be disposed within an outflow lumen of the device. In yet another embodiment, the flow meter can be disposed external to the device but along the flow path between gas/fluid source 122 and the ablation device. The flow meter can be configured to measure and report a flow rate of fluid/gas or vapor as it moves through or exits the uterine ablation device. The read out mechanism can be numerical, graphical, or icon based. Other variations include various audio and visual signals, indicia, qualitative indicia, alarms, and color identifiers. A filter may or may not be attached to the flow meter.

Figure 3:
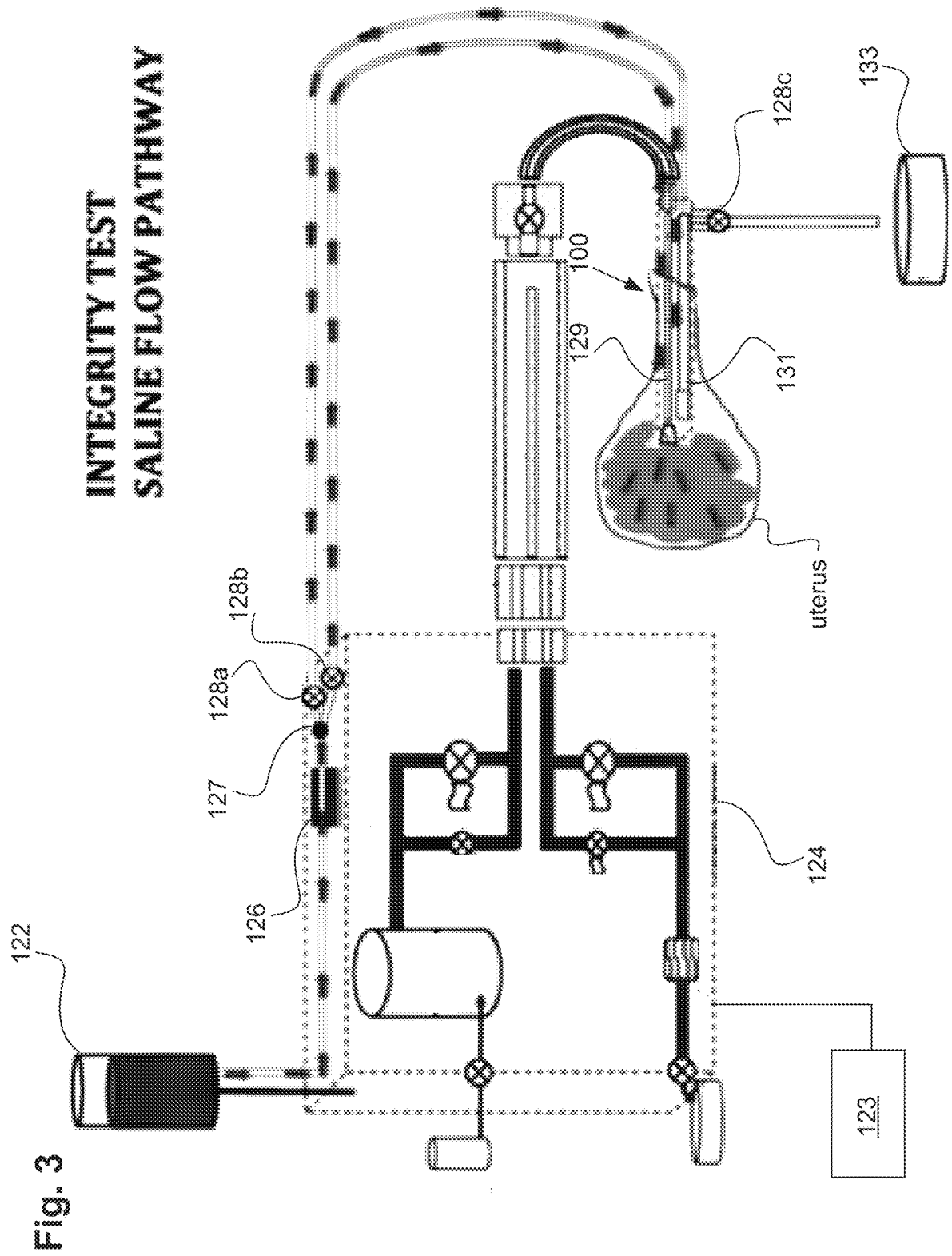
FIG. 3 illustrates an integrity test of the uterine ablation device.

Referring to FIGS. 2 and 3, to perform a uterine integrity test, gas, such as $CO_2$, or a fluid, such as saline, can be delivered from the gas/fluid source 122, through a pressure regulator, and through a flow meter 126 into the uterine ablation device 100. As shown in FIG. 3, the gas/fluid can be delivered into the uterus via both inflow lumen 129 and outflow lumen 131. In one specific embodiment, a saline such as 0.9% NaCl can be delivered into the uterus during a uterine integrity test, to determine whether there are leaks in the uterus or cervical canal through which vapor could escape during an ablation procedure. The uterine ablation device 100 can be coupled to an energy generator 124 and controller 123 for uterine ablation therapy. The vapor generator can be, for example, a vapor generator (as shown), but can also be any other type of energy generator, such as an RF energy generator, a cryotherapy generator, etc. Any type of energy modality can be used to ablate or treat the uterus after performing the integrity and patency tests described herein.

In one embodiment, a one way valve 127 as seen in FIG. 3 can be located between the flow meter 126 and the uterine ablation device 100. In other variations the one way valve 127 can be located in the handle of the uterine ablation device 100 as well as other components such as the flow meter 126 and valves 128a, 128b, and 128c. The one way valve can reduce or eliminate retrograde flow of saline during uterine contractions. The one way valve is characterized as providing low resistance to flow in one direction (towards the uterine cavity) and high resistance to flow in the retrograde direction (towards the gas/fluid source). Advantageously the one way valve can stabilize flow values because retrograde flow values are eliminated. By reducing the sinusoidal wave patterns that can be caused by uterine contractions or relaxations, movements by the patient, or inadvertent manipulations of the inflow line or the patient herself by the physician or medical staff, the procedure time is reduced. This filtering out of negative flow values isolates positive components of flow, reduces noise in flow rate values, thereby accelerating the interpretation of flow rate data and reducing procedural time.

A controller of the uterine ablation device, either integrated into the device or into the vapor generator coupled to the device, can be configured to open and close valves 128a, 128b, and 128c to allow gas or fluid to flow from source 122 into the inflow and outflow lumens 129 and 131 of the ablation device 100. Valves 128a, 128b, and 128c can be any type of valve known in the art, such as solenoid valves, inflatable balloons, air cylinders, or electric/hydraulic actuators or cams and gears. During a uterine integrity test, the controller can be configured to open valves 128a and 128b and close valve 128c, to prevent passage of gas/fluid into the waste container 133. This allows gas or fluid to flow from source 122, through flow meter 126, through one way valve 127 and valves 127a and 128b, and into inflow lumen 129 and outflow lumen 131. As the gas or fluid enters the uterus, the flow meter can measure an integrity flow rate of the gas or fluid.

In one embodiment, the controller of the uterine ablation device or the vapor generator can run an integrity test algorithm to determine if the uterus is sealed. The algorithm can analyze integrity flow rate data from the flow meter during the integrity test as gas/fluid is delivered into the uterus. Specifically, the algorithm can analyze a maximum flow rate and a minimum flow rate during an integrity test time window. The integrity test time window can be, for example, a rolling time window of a pre-selected duration. In one specific embodiment, the algorithm analyzes a maximum flow rate and a minimum flow rate continuously during a rolling 15-second integrity test time window. For each rolling integrity test time window, the minimum and maximum flow rates can be calculated. The difference between the minimum and maximum flow rates in each integrity test time window can be calculated to yield a delta flow value (maximum flow rate minus minimum flow rate), which can be used as an indicator of the stability of flow. For example, the larger the delta flow value, the less stable the flow of gas/fluid, and the smaller the delta flow value, the more stable the flow of gas/fluid. If the maximum flow rate and the delta flow value of gas or fluid stabilizes below an integrity threshold value, the controller can determine that the uterus is sealed. Importantly, the test is comprised of two algorithms that compare flow to an integrity threshold value concurrently with a second algorithm that compares the delta flow value to the integrity threshold value, and uses both of these comparisons to determine the ultimate outcome of the integrity test. The application of both of these comparisons provides greater sensitivity in the test results.

In some embodiments, this integrity flow rate delta threshold value can be approximately 5 ml/min. Therefore, in some embodiments, a uterus is considered to "pass" the uterine integrity test if both the maximum flow rate and the integrity flow rate delta threshold value are below 5 ml/min over a rolling integrity test time window. Alternatively, the test can include different thresholds for maximum flow rate and the delta flow value.

In some embodiments, the uterine integrity test can run for a pre-set time period. For example, the test can run for 60 seconds, and subsequent rolling 15-second windows can be analyzed to determine if the uterus is sealed during the 60 second time period. In another embodiment, the delta flow value can be defined as a standard deviation of the average flow that is compared to a threshold value. This delta flow value can then be compared to the threshold value to determine if the uterus is sealed.

In some embodiments, the return channel comprises a valve 128c, such as a solenoid valve, air cylinder, electric/hydraulic actuators, cams and gears or pump/inflatable balloon, which can be activated upon the start of the integrity test to close off the egress of the gas/fluid through the return channel of the uterine ablation device. When the return flow of gas/fluid through the return channel is stopped with the valve, a change of flow can be detected by the flow meter 126 on the input line. In addition to determining if there is a leak or if the device is positioned properly, the specifics of the changes in flow (e.g., how the flow reacts to closing of the return line with the valve) can provide the following the indications in some cases: a) the size of the uterine cavity; and b) the presence of a leak or lack of integrity in the system. For instance in clinical use with uteri of varying sizes, an integration under the graphical curve of flow rate versus time provides a volume assessment of the size of uterine cavity. The amount of volume can provide the physician information not only on the size of the uterus, but whether the device is improperly embedded in a false passage (smaller volume amount) or in the peritoneal cavity (larger volume amount).

Figure 4:
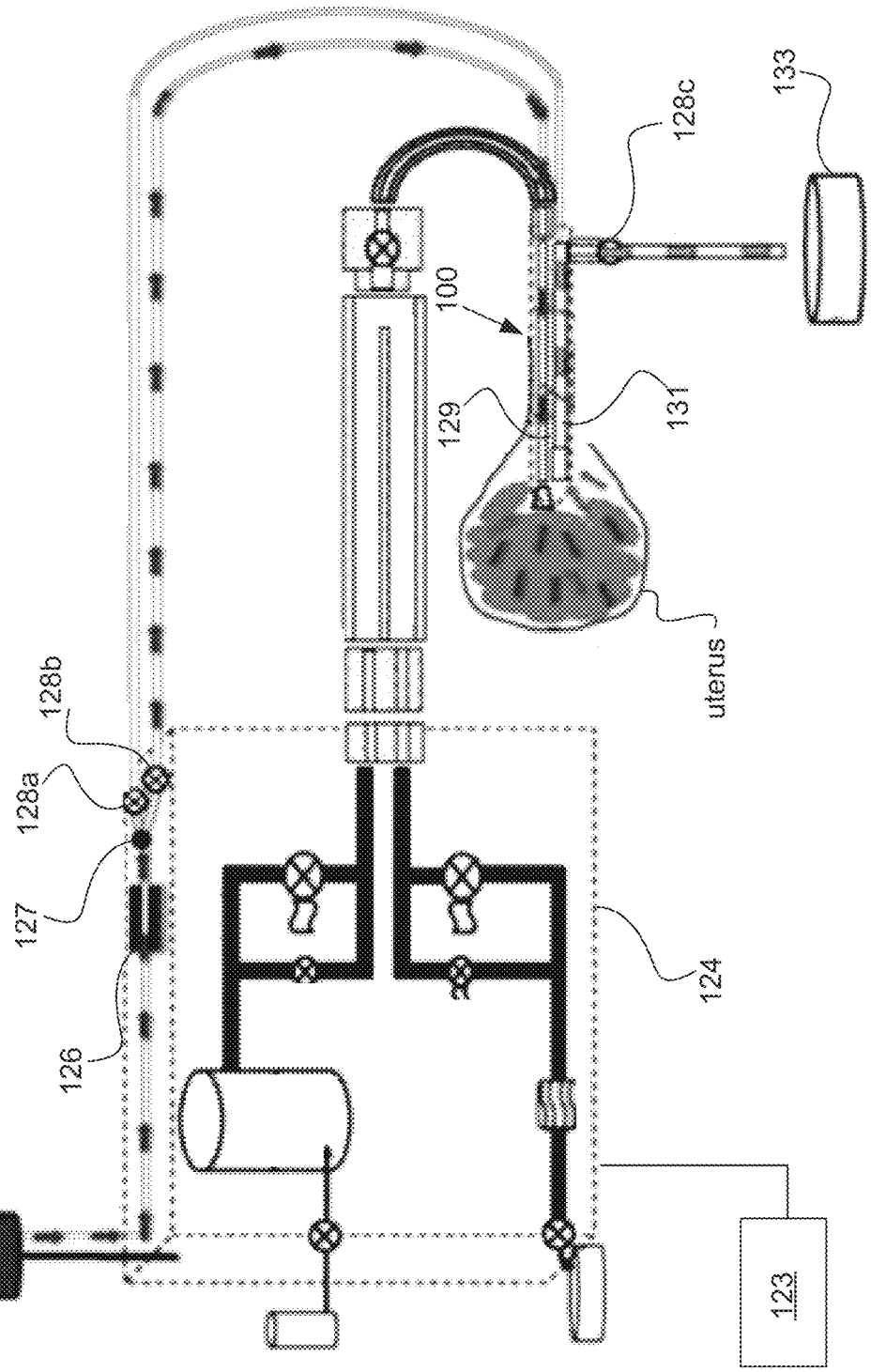
FIG. 4 illustrates a patency test of the uterine ablation device.

Immediately after performing the integrity test above, the amount of flow in the inflow and outflow channels can be measured in a patency test and used to determine the presence of an obstruction that may affect the flow of vapor during the ablation procedure. Based on this determination or patency test, the device may be repositioned or replaced prior to delivery of vapor. For example, in one embodiment, referring to FIG. 4, a method of performing a patency test can comprise delivering gas or fluid from inflow lumen 129 of the uterine device into the uterus, also referred to as the fluid infusion tip, removing gas or fluid from the uterus with outflow lumen 131 of the uterine device, also referred to as the fluid outflow tip, and determining that the uterine device is not clogged or embedded in tissue if a flow rate of gas or fluid is observed in the flow meter of the inflow lumen of the uterine device. In FIGS. 3-4, valves 128a and 128b control the flow of gas/fluid to the uterine ablation device 100 and valve 128c control the flow of gas/fluid from the outflow lumen 131 into the outflow canister or waste container 133. Control of the valves 128a and 128b and 128c can be performed by a separate controller and software unit shown as 123.

If it has been determined that the uterus is sealed based on the integrity test performed and described in FIG. 3, the controller can also be configured to perform a patency test. In one embodiment, referring to FIG. 4, the controller can be configured to open valves 128b and 128c, but close valve 128a. This allows gas or fluid to flow from source 122, through flow meter 126, through one way valve 127 and valve 128b, and into inflow lumen 129. Gas or fluid can be removed through outflow lumen 131, through valve 128c, and into a waste container 133. As the gas or fluid enters and is removed from the uterus, the flow meter can measure a patency flow rate of the gas or fluid. If the patency flow rate is maintained above a patency flow rate threshold value, the controller can determine that the device is not clogged or embedded into tissue. In some embodiments, observing or measuring a flow of fluid or gas in outflow lumen 131 can be used to determine that the device is not clogged or embedded in tissue. A flow rate above a patency test threshold during a rolling patency test time window can indicate that the lumens are not clogged or that the distal end of the uterine ablation device is not embedded into tissue.

In one specific embodiment, the patency test threshold can be greater than 5 ml/min, and the rolling patency test time window can be a 5 second time period. Thus, the flow meter can measure the patency flow rate in rolling patency time windows (e.g., rolling 5 second periods) and the controller can analyze the measured rate. If the patency flow rate is maintained above the patency test threshold (e.g., 5 ml/min) during a rolling patency time window, then the patency test is considered passed and the test can be stopped. Passing the patency test indicates that the uterine ablation device is not obstructed or placed in false passage. If the patency test threshold is not satisfied, the physician should repeat the insertion steps and/or repeat the integrity test and patency test prior to initiating uterine ablation. When the patency flow rate is below the threshold of 5 ml/min during the rolling patency test time window, the uterine ablation device may need to be repositioned.

During the transition from the end of integrity test to the start of the patency test, the uterine cavity can be substantially filled with the gas/fluid provided during the integrity test. As described above, the closed outflow valve during the integrity test prevents gas or fluid from exiting the uterine cavity into the waste container 133. In one embodiment, it is desirable for valve 128c to be opened only partially in the range of 20-50% open for a flow rate greater than 5 ml/min and less than 40 ml/min so the uterine cavity distension achieved during the integrity test is temporarily maintained when the patency test checks for open flow through the uterine ablation device. Certain types of valves are better suited for partial opening. For example, balloon valves can be pulsed at various duty cycles to partially open the valve. The higher the duty cycle, the more quickly the valve can be opened. Partial opening of the valve prevents the uterine cavity from collapsing too quickly around the tip of the uterine ablation device which, in some instances, may cause a false positive failure of the patency test. In one embodiment, partial opening of the valve can be achieved by pulsing the opening of the valve at a specified duty cycle until flow through the vapor probe begins, or alternatively until the uterine pressure begins to drop. In another embodiment, the valve 128c can be opened rapidly just until flow through the valve begins. This rapid drop opening of the valve can be achieved by pulsing the valve initially with a high duty cycle, then shortening the pulsing (or lowering the duty cycle) as the valve approaches the range where flow through the valve begins. Once the patency flow rate increases above a threshold (or by a specific rate of increase), the valve can be maintained.

In one specific embodiment, the valve 128c can be a balloon filled to as much as 20 psig to occlude the tubing leading to waste container 133. The balloon valve can be pulsed open for up to 40 msec every 200 msec until the balloon pressure falls to as low as 5 psig. The valve opening time can then be reduced even further until the balloon pressure falls to between 3-4 psig. The valve can continue to be pulsed until flow increases to a level of 0.20 ml/min or until flow rises above the threshold value (e.g., above 5 ml/min).

Figure 5:
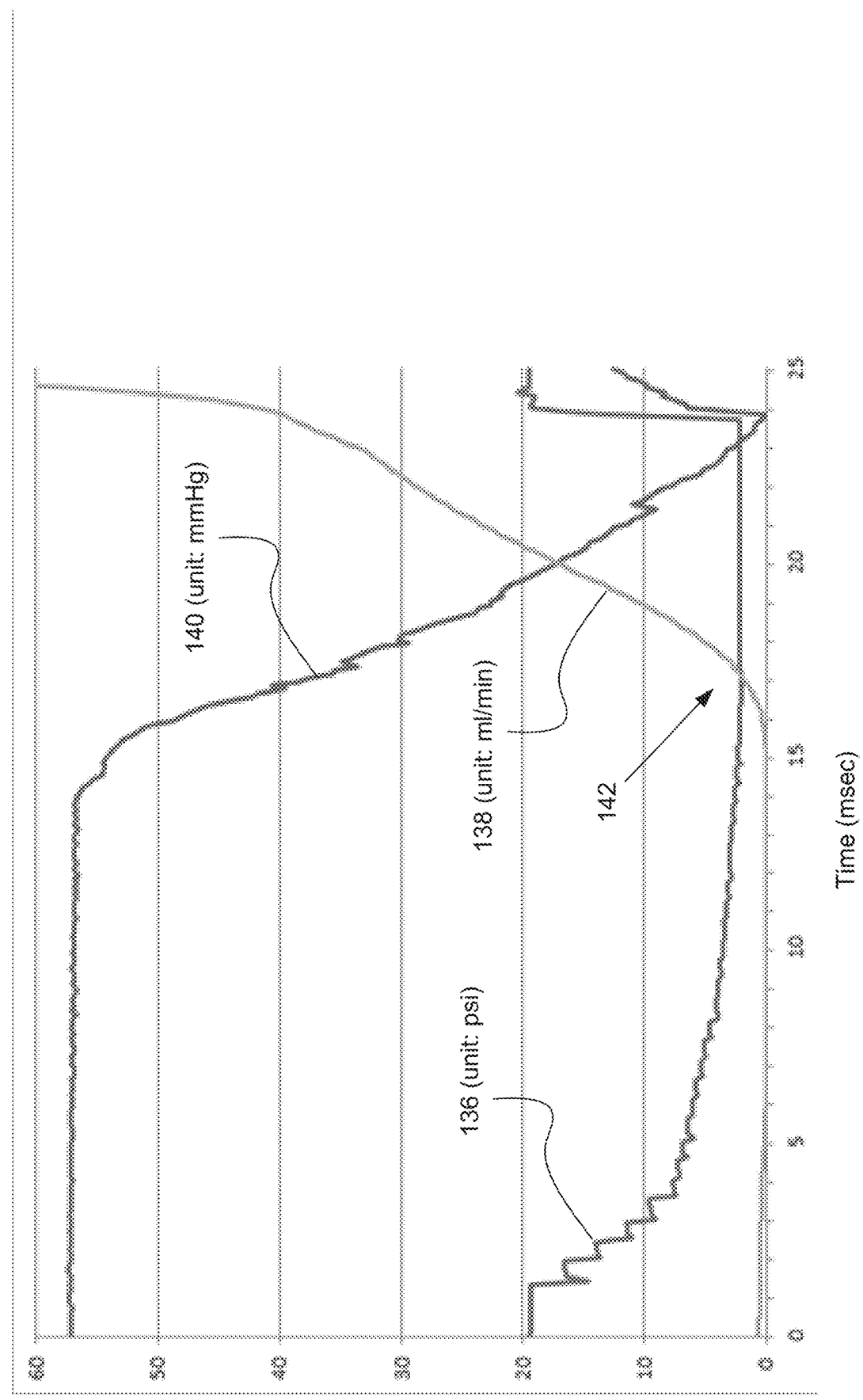
FIG. 5 charts the relationship between outflow valve pressure, uterine cavity pressure, and flow through a uterine ablation device.

FIG. 5 shows one specific embodiment where the outflow valve (e.g., valve 128c from FIG. 3) comprises an inflatable balloon. Inflating the balloon causes obstruction of the outflow lumen of the uterine ablation device, and deflating the balloon allows flow out of the device and into the waste container. FIG. 5 shows the outflow valve pressure 136 (mmHg), the flow 138 (ml/min) through the uterine ablation device, and the uterine cavity pressure 140 (mmHg) during a typical patency test. At the completion of a typical integrity test, the cavity pressure should be above 52 mmHg, the outflow valve pressure about 20 psi, and the flow through the uterine ablation device close to zero. In the first few seconds of the patency test, the outflow valve pressure decreases rapidly, then the rate of deflation decreases to zero as flow through the device begins, shown by arrow 142. The cavity pressure drops gradually as flow increases. The patency algorithm can run concurrently with deflation of the outflow valve. In some embodiments, the deflation period of the outflow valve is typically from 3 to 40 msec.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A uterine ablation device, comprising:
   a shaft adapted to be inserted into a uterus of a patient, the shaft including an outflow lumen and an inflow lumen;
   a source configured to deliver gas or fluid through the inflow lumen of the shaft into the uterus;
   an outflow valve configured to seal the outflow lumen of the shaft;
   a flow meter that is fluidly coupled to the inflow lumen and configured to measure a flow rate of gas or fluid as it is delivered into the uterus; and
   an electronic controller operatively coupled to the source, the outflow valve, and the flow meter, the electronic controller being configured to:
      open the outflow valve only partially to remove gas or fluid from the uterus through the outflow lumen of the uterine ablation device while maintaining distension of a cavity of the uterus;
      determine a flow rate of gas or fluid in the outflow lumen while the outflow valve is only partially opened and distension of the cavity of the uterus is maintained; and
      determine that the uterine ablation device is not clogged or embedded in tissue if the flow rate of gas or fluid is above a threshold value.

2. The device of claim 1, wherein the threshold value is 5 ml/min.

3. The device of claim 1, wherein the electronic controller is configured to determine that the uterine ablation device is not clogged or embedded in tissue if the flow rate of gas or fluid measured by the flow meter is above the threshold value during a rolling patency test time window.

4. The device of claim 3, wherein the rolling patency test time window is a 5 second time period.

5. The device of claim 1, wherein the outflow valve is partially opened in a range of 20% to 50% open when the flow rate is determined.

6. The device of claim 1, wherein the outflow valve comprises a balloon valve.

7. The device of claim 6, wherein the outflow valve is partially opened by pulsing the opening of the outflow valve at a specified duty cycles.

\* \* \* \* \*